United States Patent
Yamasita et al.

[11] Patent Number: 6,159,242
[45] Date of Patent: Dec. 12, 2000

[54] INTRAOCULAR LENS HAVING SUPPORT MEMBER FIXED IN HOLE FORMED IN INSERT EMBEDDED IN LENS BODY, AND METHOD OF PRODUCING THE SAME

[75] Inventors: Keiji Yamasita, Nagoya; Tatsuya Ojio, Kasugai; Tohru Kawaguchi, Gifu, all of Japan

[73] Assignee: Menicon Co., Ltd., Nagoya, Japan

[21] Appl. No.: 09/226,958

[22] Filed: Jan. 8, 1999

[30] Foreign Application Priority Data

Jan. 16, 1998 [JP] Japan .................. 10-006260

[51] Int. Cl.$^7$ ...................................................... A61F 2/16
[52] U.S. Cl. ............................................................. 623/6.46
[58] Field of Search ...................... 623/6.46, 6.38–6.45, 623/6.47–6.55

[56] References Cited

U.S. PATENT DOCUMENTS

| | | | |
|---|---|---|---|
| 4,139,915 | 2/1979 | Richards et al. | 623/6.46 |
| 4,155,125 | 5/1979 | Woodcock et al. | 623/6.46 |
| 4,790,846 | 12/1988 | Christ et al. | |
| 5,133,746 | 7/1992 | Brady et al. | |
| 5,141,507 | 8/1992 | Parekh | 623/6.46 |
| 5,171,268 | 12/1992 | Ting et al. | |
| 5,252,262 | 10/1993 | Patel | |
| 5,306,297 | 4/1994 | Rheinish et al. | |
| 5,578,078 | 11/1996 | Nakajima et al. | |

FOREIGN PATENT DOCUMENTS

| | | |
|---|---|---|
| 5-56988 | 3/1993 | Japan |
| 6-24543 | 4/1994 | Japan |
| 7-503148 | 4/1994 | Japan |

*Primary Examiner*—David H. Willse
*Attorney, Agent, or Firm*—Burr & Brown

[57] ABSTRACT

A method of producing an intraocular lens including a lens body, and at least one support member each of which is inserted into a mounting hole open in a circumferential surface of the lens body, the lens body being obtained by polymerization of a monomer composition in a mold assembly which defines a mold cavity having a profile following that of the lens body, the method comprising the steps of: installing a separately prepared insert member on the mold assembly such that the insert member is located within the mold assembly at a position of the mold cavity corresponding to a region of the lens body where the mounting hole is formed; polymerizing the monomer composition in the mold assembly to provide a workpiece which gives the lens body, such that the workpiece includes the insert member; obtaining the lens body from the workpiece such that at least a portion of the insert member is embedded as an insert in the region of the lens body; and forming the mounting hole in the insert.

6 Claims, 13 Drawing Sheets

INTRAOCULAR LENS HAVING SUPPORT MEMBER FIXED IN HOLE FORMED IN INSERT EMBEDDED IN LENS BODY, AND METHOD OF PRODUCING THE SAME

The present application is based on Japanese Patent Application No. 10-6260 filed Jan. 16, 1998, the content of which is incorporated hereinto by reference.

BACKGROUND OF THE INVENTION

1. Field of the Invention

The present invention relates to an intraocular lens which comprises a lens body having an optical portion, and a support member extending radially outwardly from the lens body for holding the lens body in position within the eye. The invention is also concerned with a method of producing such an intraocular lens.

2. Discussion of the Related Art

There has been known an intraocular lens which comprises a generally circular lens body including an optical portion, and at least one support member in the form of an elongate thin filament, which is inserted at its one end into and fixed within a mounting hole which is open in the circumferential surface of the lens body. The support member needs to be firmly fixed to the lens body, to hold the lens body in position within the eye with high stability.

JP-A-5-56988 discloses a method of fixing the support member to the lens body, wherein an adhesive (prepolymer) is used to chemically bond the support member to the lens body by polymerization of the adhesive. JP-B-6-24543 discloses a method of fixing the support member to the lens body, wherein the support member has an anchoring portion in the form of a bulb or a loop formed at its proximal end at which the support member is fixed to the lens body. The anchoring portion of the support member is embedded in the lens body, to thereby fix or anchor the support member to the lens body. JP-A-7-503148 discloses a method of fixing the support member to the lens body, by inserting the proximal end portion of the support member in a fixing hole formed in the lens body, and laser-welding the support member, so that the support member is fixed to the lens body.

The method disclosed in JP-A-5-56988 suffers from a problem of a residual monomer after the support member has been bonded to the lens body, which residual monomer would arise from the use of the prepolymer as an adhesive. Accordingly, this method gives rise to a problem of insufficient safety. In addition, it is difficult to prepare the adhesive, and determine the amount of the adhesive to be used. In the method of JP-B-6-24543, it is difficult to form the anchoring portion having a predetermined shape at the proximal end portion of the support member, making the fabrication of the intraocular lens cumbersome. In the method of JP-A-7-503148, there is a risk that the material, shape, and mechanical strength of the lens body which includes the optical portion may be adversely influenced by the laser beam used in welding the support member, for fixation thereof to the lens body. Accordingly, none of those disclosed methods are satisfactory, and there has been a need for an improved method of fixing the support member to the lens body.

SUMMARY OF THE INVENTION

It is therefore a first object of the present invention to provide a method of producing an intraocular lens comprising a lens body and a support member, wherein the support member can be easily and firmly fixed to the lens body with high efficiency without adversely influencing the lens body.

It is a second object of the present invention to provide an intraocular lens having a novel structure which is not deteriorated in the process of manufacture.

The above first object of the invention may be attained according to a first aspect of the invention, which provides a method of producing an intraocular lens including a lens body, and at least one support member each of which is inserted into a mounting hole open in a circumferential surface of the lens body, the lens body being obtained by polymerization of a monomer composition in a mold assembly which defines a mold cavity having a profile following that of the lens body, the method comprising the steps of: installing a separately prepared insert member on the mold assembly such that the insert member is located within the mold assembly at a position of the mold cavity corresponding to a region of the lens body where the mounting hole is formed; polymerizing the monomer composition in the mold assembly to provide a workpiece which gives the lens body, such that the workpiece includes the insert member; obtaining the lens body from the workpiece such that at least a portion of the insert member is embedded as an insert in the region of the lens body; and forming the mounting hole in the insert.

In the intraocular lens produced according to the present method, the insert member which has been prepared separately from the lens body is at least partly embedded as an insert in the lens body which includes the optical portion, and the support member is fixed to the embedded insert. In other words, the support member is fixed with respect to the lens body, i.e., a polymer that constitutes the optical portion of the lens body, via an embedded portion of the separately prepared insert member formed of a polymer different from that of the lens body. Accordingly, when the monomer composition is polymerized in the mold assembly to produce the workpiece, the insert is impregnated with the monomer composition, so that the monomer composition is absorbed by or swollen in the insert, whereby the insert is integrally fixed or bonded to the lens body without applying a bonding adhesive therebetween.

According to the present arrangement, the support member is not directly fixed to the polymer which constitutes the optical portion of the lens body. Therefore, this arrangement minimizes or prevents adverse influences on the optical portion of the lens body, which would be caused when the support member was directly fixed to the lens body. Further, the material of the insert member (i.e., the insert) can be freely determined, irrespective of the material giving the polymer which constitutes the optical portion, so that the support member can be easily and firmly fixed with respect to the lens body.

In a first preferred form of the above first aspect of the present invention, the insert member is installed on the mold assembly such that only an inner portion of the insert member is inserted as the insert in a peripheral portion of the mold cavity. In this arrangement, the insert member is supported on the mold assembly at its outer portion which is located outside the mold cavity, permitting easy installation of the insert member on the mold assembly. Accordingly, the above-indicated inner portion of the insert member is easily placed in position within the mold cavity, whereby the molding efficiency of the workpiece is improved.

In a second preferred form of the above first aspect of the present invention, the step of obtaining the workpiece comprises a step of cutting an outer surface of the workpiece obtained by polymerization of the monomer composition in the mold assembly, so as to remove the insert member except the insert, and such that the circumferential surface of the lens body is exposed.

According to this arrangement, the exposed outer surface (cut surface) of the insert which is integrally embedded in the lens body is flush with the outer circumferential surface of the workpiece including the lens body, without an exclusive step of cutting the insert member per se. In particular, when the insert member is installed on the mold assembly such that its inner portion extends into the mold cavity that gives the lens body, the outer portion of the insert member which is located outside the mold cavity is removed when the outer portion of the workpiece is removed by a cutting operation. Thus, the present arrangement eliminates an exclusive step of cutting the unnecessary outer portion of the insert member which is located outside the mold cavity, resulting in improved fabrication efficiency of the intraocular lens. In an alternative arrangement, the outer portion of the insert member remains unremoved, so that it protrudes from the periphery of the lens body by a suitable distance. In this case, the outer portion of the insert member in addition to the inner portion serving as the embedded insert permits the support member to be fixed over a sufficiently large length.

In a third preferred form of the above first aspect of the present invention, the mounting hole in which the support member is inserted is bored in the insert embedded in the lens body. According to this arrangement, the mounting hole is bored only within the material of the insert.

In a fourth preferred form of the above first aspect of the present invention, the insert member includes a hollow structure having a hole which provides the mounting hole. According to this arrangement, the mounting hole is formed when the workpiece is produced by the polymerization of the monomer composition in the mold assembly, resulting in improved productivity of the intraocular lens. In this case, the hole which provides the mounting hole is formed in at least a portion of the insert member (hollow structure), which portion is to be integrally embedded in the lens body as the insert. Though the size or inside diameter of the mounting hole is not particularly limited, it is suitably determined depending upon the outer dimension or outside diameter of the support member. Generally, the inside diameter of the mounting hole is in a range of 0.05 mm–0.4 mm.

The insert member has a configuration which is suitable for desired positioning within the mold assembly. The material of the insert member is not particularly limited, but is preferably determined by taking account of the required strength of adhesion to the workpiece. It is preferable to use a synthetic resin material, generally, a copolymer. Examples of the copolymer include polyalkyl methacrylate such as crosslinked or non-crosslinked polymethyl methacrylate (PMMA) and polyethyl methacrylate; polyvinylidene fluoride; polypropylene; and polyethylene terephthalate.

The material of the monomer composition that gives the workpiece by polymerization is not particularly limited, but may be suitably selected from among any known monomers such as: methacrylate or acrylate monomers which include alkyl methacrylate, alkyl acrylate, fluorine-containing alkyl methacrylate, fluorine-containing alkyl acrylate, aromatic-ring-containing methacrylate, and aromatic-ring-containing acrylate; styrene derivatives; imide-group-containing monomers; and N-vinylactams. When the workpiece which gives the lens body is formed of a soft material such as a polymer which is obtained by polymerization of the monomer composition which contains alkyl acrylate as an essential component, the intraocular lens to be obtained from the workpiece can be easily handled during a surgical operation to insert the intraocular lens in the eye of the patient.

When the workpiece that gives the lens body is formed of the soft material described above, the insert member is preferably formed of a material which is harder than that of the workpiece. In this arrangement, the mounting hole in which the support member is inserted can be easily formed in the insert by drilling, for example, even when the workpiece that gives the lens body including the optical portion is formed of a considerably soft material. Accordingly, the support member can be fixed to the lens body via the insert with high stability and high efficiency.

The insert member is preferably formed of a material which can be melted or deformed by application of an external energy such as heat or light. When the insert member is formed of such a material, the support member can be easily heat-welded to the insert which has the mounting hole.

Although the support member may be fixed, by caulking, or by using a bonding adhesive, to the insert in which the mounting hole is formed, it is preferable that the support member be fixed to the insert by heat-welding with the support member being inserted in the mounting hole formed in the insert. According to this arrangement, the support member can be easily and firmly fixed to the lens body via the embedded insert with high stability and efficiency, whereby the intraocular lens can be fabricated with high efficiency.

When the support member is fixed to the lens body in such a manner that the support member is heat-welded to the insert which is embedded in the lens body, the insert member can be formed of a copolymer which is not chemically bonded to the support member. This arrangement avoids the problem of the residual monomer conventionally experienced when the support member is fixed to the lens body by using the adhesive such as a prepolymer. Accordingly, the intraocular lens to be obtained enjoys a sufficiently high degree of safety. The support member is heat-welded to the insert which is integrally embedded in the lens body by using a laser beam, for instance. Preferably, the support member is heat-welded to the insert by using a heating device having a pointed heat-generating portion. Described in detail, the pointed heat-generating portion of the heating device is held in contact with the lens body, so that the heat is transmitted to the support member which is inserted in the mounting hole formed in the insert.

When the support member is heat-welded to the insert integrally embedded in the lens body for fixation thereto, it is desirable that at least the support member, preferably both of the support member and the insert be formed of a thermoplastic copolymer. In particular, the support member is preferably formed of polyalkyl methacrylate, polypropylene, polyimide, or polyvinylidene fluoride.

The present method is applicable when the intraocular lens is fabricated by forming a rod-shaped or a cylindrical lens blank which gives a plurality of lens bodies, and cutting the lens blank into a plurality of pieces each having a suitable axial dimension, so that a plurality of intraocular lenses are obtained from the respective pieces. Preferably, the present method uses the mold assembly which has a single mold cavity that gives a single lens body by polymerization of the monomer composition in the mold cavity. In this case, the insert member comprises an outer portion and at least one plate-shaped inner portion each of which has a thickness smaller than that of the lens body, the insert member being installed on the mold assembly such that the at least one plate-shaped inner portion extends into an axially intermediate portion of the mold cavity. According to this arrangement, the surface area of the insert which is to be held in contact with the lens body is made sufficiently large, whereby the insert is embedded in the lens body with high stability.

The above second object of the present invention may be attained according to a second aspect of the invention, which provides an intraocular lens including a lens body having an optical portion at its central portion and a support member partly inserted into a mounting hole which is open in a circumferential surface of the lens body, so that the support member is fixed with respect to the lens body, wherein the improvement comprises: the lens body including an insert embedded therein such that the insert is exposed to the circumferential surface of the lens body, the mounting hole being formed in the insert.

In the intraocular lens produced according to the above second aspect of the invention, the support member is fixed indirectly to the lens body including the optical portion, via the insert which is integrally embedded in the lens body. This arrangement advantageously prevents or minimizes adverse influences on the optical portion, which would be caused when the support member was directly fixed to the lens body. Further, the material of the insert can be freely selected, regardless of the material of the lens body including the optical portion. Accordingly, in the present intraocular lens, the support member can be easily and firmly fixed to the lens body via the insert integrally embedded therein without a risk of deteriorating the optical properties of the optical portion.

The material of the insert is preferably selected from among any known copolymers. The polymer which constitutes the lens body including the optical portion is obtained at the same time when the lens body is molded by polymerization. Alternatively, the polymer which has been polymerized can be used as the material for the lens body.

The insert is integrally embedded in the lens body by chemically bonding it to the lens body during or after molding of the lens body, or by using a bonding adhesive. In addition, or in place of, such a bonding method, the insert may be provided with anchoring means by which the insert is prevented from being removed from the lens body. This anchoring means is effective to mechanically fix the insert to the lens body, whereby the insert is firmly embedded in the lens body with high stability.

BRIEF DESCRIPTION OF THE DRAWINGS

The above and optional objects, features, advantages and technical significance of the present invention will be better understood by reading the following detailed description of presently preferred embodiments of the invention, when considered in conjunction of the accompanying drawings, in which.

DETAILED DESCRIPTION OF THE PREFERRED EMBODIMENT

Figure 1:
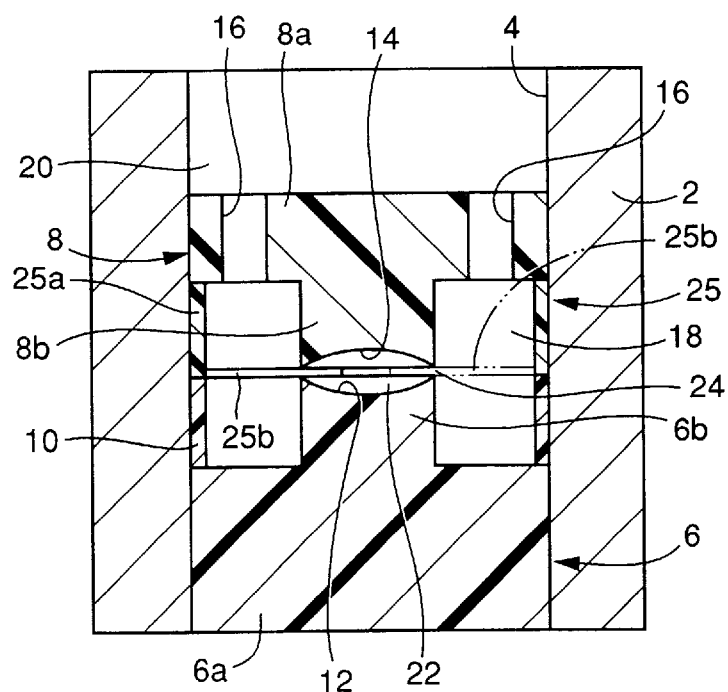
FIG. 1 is an elevational view in longitudinal or axial cross section of a mold assembly including upper and lower mold halves, which are closed together within a cylindrical body, for forming an intraocular lens according to a method of the present invention.

Referring first to FIG. 1, there is shown a mold assembly which is used in producing an intraocular lens according to the present invention. The mold assembly includes a cylindrical body 2 having an inner bore 4, a lower mold half 6, and an upper mold half 8. Within the inner bore 4 of the cylindrical body 2, the lower and upper mold halves 6, 8 are positioned so as to oppose to each other with a suitable axial distance therebetween.

The lower mold half 6 includes a cylindrical base portion 6a with a relatively large diameter, and an upper cylindrical molding portion 6b with a relatively small diameter, which protrudes from a central part of the upper surface of the cylindrical base portion 6a in the axially upward direction, as seen in FIG. 1. The end face of the upper cylindrical molding portion 6b is formed to serve as a lower molding surface 12 having a contour following that of one of the opposite surfaces of a lens body of an intended intraocular lens. With the thus constructed lower mold half 6 being fitted in the inner bore 4 of the cylindrical body 2, a lower annular spacing is defined between the outer circumferential surface of the upper cylindrical molding portion 6b of the lower mold half 6 and the corresponding portion of the inner circumferential surface of the cylindrical body 2. The cylindrical base portion 6a of the lower mold half 6 is fluid-tightly fitted in the inner bore 4, to thereby close the lower open end of the inner bore 4.

The upper mold half 8 has a cylindrical base portion 8a with a relatively large diameter, and a lower cylindrical molding portion 8b protruding from a central part of the lower surface of the cylindrical base portion 8a in the axially downward direction, as seen in FIG. 1. The end face of the lower cylindrical molding portion 8b is formed to serve as an upper molding surface 14 having a contour following that of the other surface of the lens body of the intended intraocular lens. With the thus constructed upper mold half 8 being fitted in the inner bore 4 of the cylindrical body 2, an upper annular spacing is defined between the outer circumferential surface of the lower cylindrical molding portion 8b of the upper mold half 8 and the corresponding portion of the inner circumferential surface of the cylindrical body 2.

The upper mold half 8 is positioned within the inner bore 4 of the cylindrical body 2 relative to the lower mold half 6, such that the upper molding surface 14 of the upper mold half 8 is opposed to the lower molding surface 12 of the lower mold half 6 with a suitable axial distance therebetween. The cylindrical base portion 8a of the upper mold half 8 has eight axial through-holes 16 formed through the thickness thereof, which through-holes 16 are equiangularly spaced apart from each other in the circumferential direction of the cylindrical base portion 8a. It is desirable to form at least three through-holes 16 in the cylindrical base portion 8a, to permit a sufficient flow of a monomer composition via the through-holes 16 into a mold cavity 22 described below, so that a workpiece to be obtained does not suffer from any defects due to shrinkage of the monomer composition during its polymerization.

In the thus constructed mold assembly, an upper chamber 20 for accommodating the monomer composition is defined by the upper surface of the cylindrical base portion 8a of the upper mold half 8 and the corresponding upper end portion of the cylindrical body 2, while an annular intermediate chamber 18 is defined by the upper and lower surfaces of the respective cylindrical base portions 6a and 8a, the circumferential surfaces of the respective cylindrical molding portions 6b and 8b, and the corresponding axial portion of the cylindrical body 2. The annular intermediate chamber 18 is to be filled with the monomer composition supplied from the upper chamber 20 through the through-holes 16. In this mold assembly, the lower molding surface 12 of the lower mold half 6 and the upper molding surface 14 of the upper mold half 8 cooperate with each other to define the mold cavity 22 having a profile corresponding to that of the lens body of the intended intraocular lens. As shown in FIG. 1, the radially peripheral portions of the two molding surfaces 12, 14 are spaced apart from each other by a relatively small axial distance, which is determined as described below. This arrangement provides the mold cavity 22 with a circumferential opening 24 through which the monomer composition flows from the intermediate chamber 18 into the mold cavity 22.

Figure 8A:
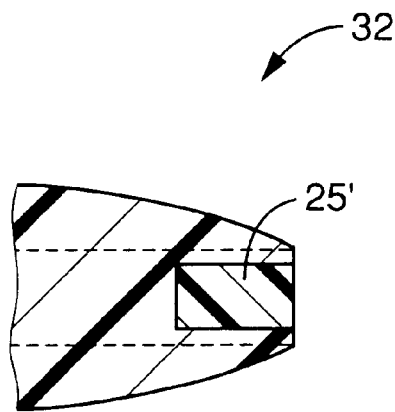
FIG. 8(a) is a fragmentary longitudinal cross sectional view showing a lens body which is obtained by cutting an intermediate product formed in the mold assembly, according to one embodiment of the present invention, the view being taken along line 8—8 of FIG. 8(b)

The materials of the mold assembly, i.e., the cylindrical body 2 and upper and lower mold halves 8, 6 are not particularly limited, as long as the materials are not adversely influenced by the monomer composition which gives, by polymerization, the workpiece from which a lens body 32 of FIGS. 8(*a*) and 8(*b*) is obtained. For instance, the cylindrical body 2 and the upper and lower mold halves 8, 6 are formed of a fluoro-resin such as polytetrafluoroethylene, an olefin resin such as polypropylene or polyethylene, a polyacetal resin, or polyethylene-terephthalate. It is desirable that the upper and lower mold halves 8, 6 are formed of a resin material which is easy to cut since the workpiece which gives the lens body 32 is obtained by cutting a polymerization product including the upper and lower mold halves 8, 6, which product is obtained after polymerization of the monomer composition within the assembly. The cylindrical body 2 may be formed of a metallic material.

Figure 2:
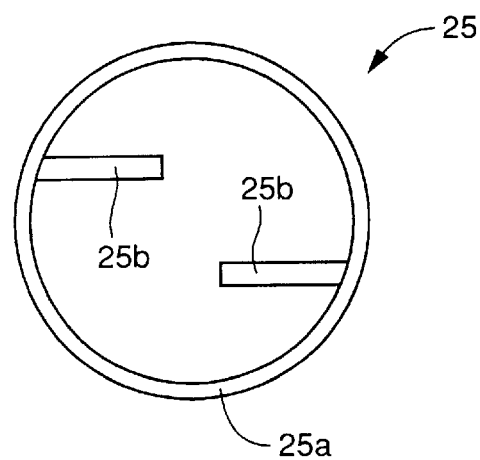
FIG. 2 is a plan view showing one example of an insert member used in the mold assembly of FIG. 1.
Figure 3:
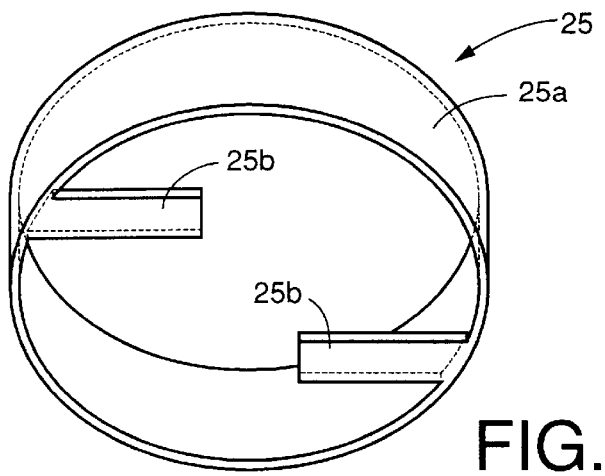
FIG. 3 is a perspective bottom view showing the insert member of FIG. 2.

In the mold assembly used according to the present embodiment, an insert member 25 is fitted in the annular intermediate chamber 18, such that the insert member 25 is interposed between the upper and lower mold halves 8, 6. As shown in FIGS. 2 and 3, the insert member 25 has an outer portion in the form of a cylindrical wall portion 25a having a small wall thickness, and a plurality of inner portions in the form of a pair of plate-like or planar inward projections 25b, 25b. The inward projections 25b, 25b are formed integrally with the outer cylindrical wall portion 25a, so as to extend inwardly from the inner circumferential surfaces of the cylindrical wall portion 25a, at the two diametrically opposite positions and at the axially lower end of the cylindrical wall portion 25a. The insert member 25 is formed of the above-described synthetic resin such as PMMA, preferably a copolymer. The insert member 25 is prepared separately from the cylindrical body 2 and the upper and lower mold halves 8, 6, by molding or machining.

The insert member 25 is superposed on a cylindrical spacer 10 which in turn is superposed on the base portion 6a of the lower mold half 6, so that the insert member 25 is sandwiched or interposed between the upper end face of the spacer 10 and the base portion 8a of the upper mold half 8. In this state, the inward projections 25b of the insert member 25 are located at the axially intermediate portion of the annular intermediate chamber 18, and extend inwardly through the annular intermediate chamber 18 into the mold cavity 22, such that the two inward projections 25b are parallel with each other, as shown in FIG. 2. As shown in FIG. 1, each inward projection 25b extends at its distal end portion through the circumferential opening 24 into the mold cavity 22 by a suitable distance.

The length of each inward projection 25b of the insert member 25 is determined such that only the distal end portion of the inward projection 25b is located within the mold cavity 22. Preferably, the length of the inward projection 25b is determined such that its distal or free end does not reach the central optical portion of the lens body 32 molded in the mold cavity 22. The axial dimension of the cylindrical wall portion 25a of the insert member 25 is determined such that the cylindrical wall portion 25a cooperates with the spacer 10 to define the axial clearance between the upper and lower mold halves 8, 6, to thereby determine an axial dimension of the mold cavity 22, namely, an axial dimension or thickness of the lens body 32 to be obtained in the mold cavity 22.

Figure 4:
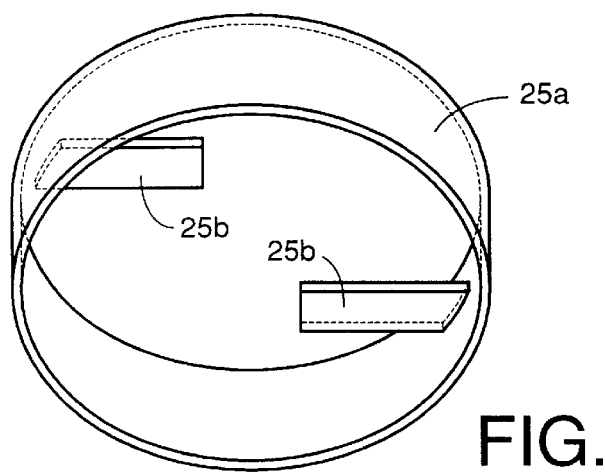
FIG. 4 is a perspective view showing another example of the insert member.
Figure 5:
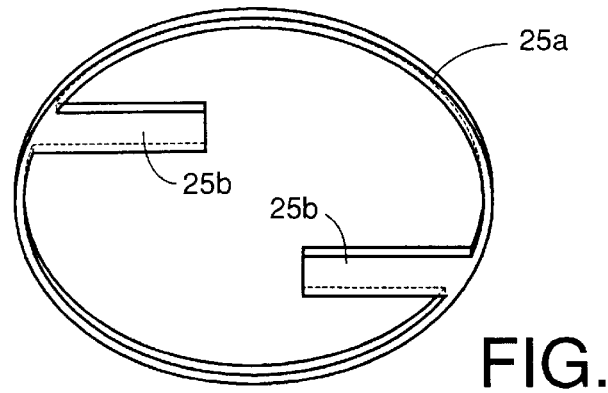
FIG. 5 is a perspective view showing still another example of the insert member.

The configuration of the insert member 25 is not limited to that illustrated in FIG. 3, but may be otherwise designed depending upon the structure of the mold assembly on which the insert member is installed. For instance, the insert member 25 may have the inward projections 25b which extend inwardly from an axially intermediate portion of the cylindrical wall 25*a* at the two diametrically opposite positions, as shown in FIG. 4. In this arrangement, the cylindrical wall portion 25*a* functions as a spacer, like the spacer 10 superposed on the base portion 6*a* of the lower mold half 6 shown in FIG. 1. Further, the axial dimension of the cylindrical wall portion 25*a* of the insert member 25 may be substantially the same as the thickness of the inward projections 25*b,* as shown in FIG. 5. The insert member 25 shown in FIG. 5 is positioned within the mold assembly of FIG. 1, such that it is sandwiched by and between two spacers disposed on its axially opposite sides, respectively.

Figure 6:
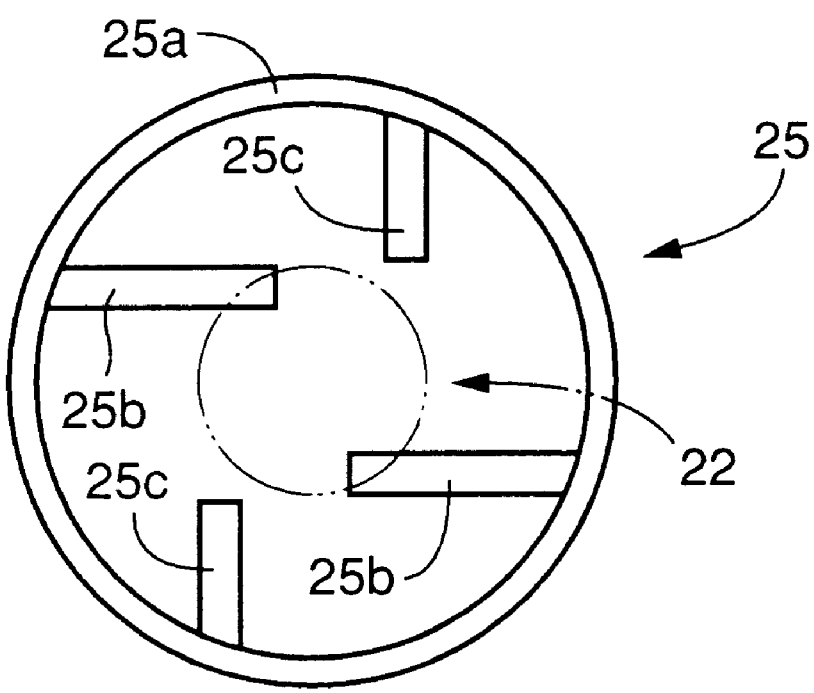
FIG. 6 is a plan view showing yet another example of the insert member.
Figure 7:
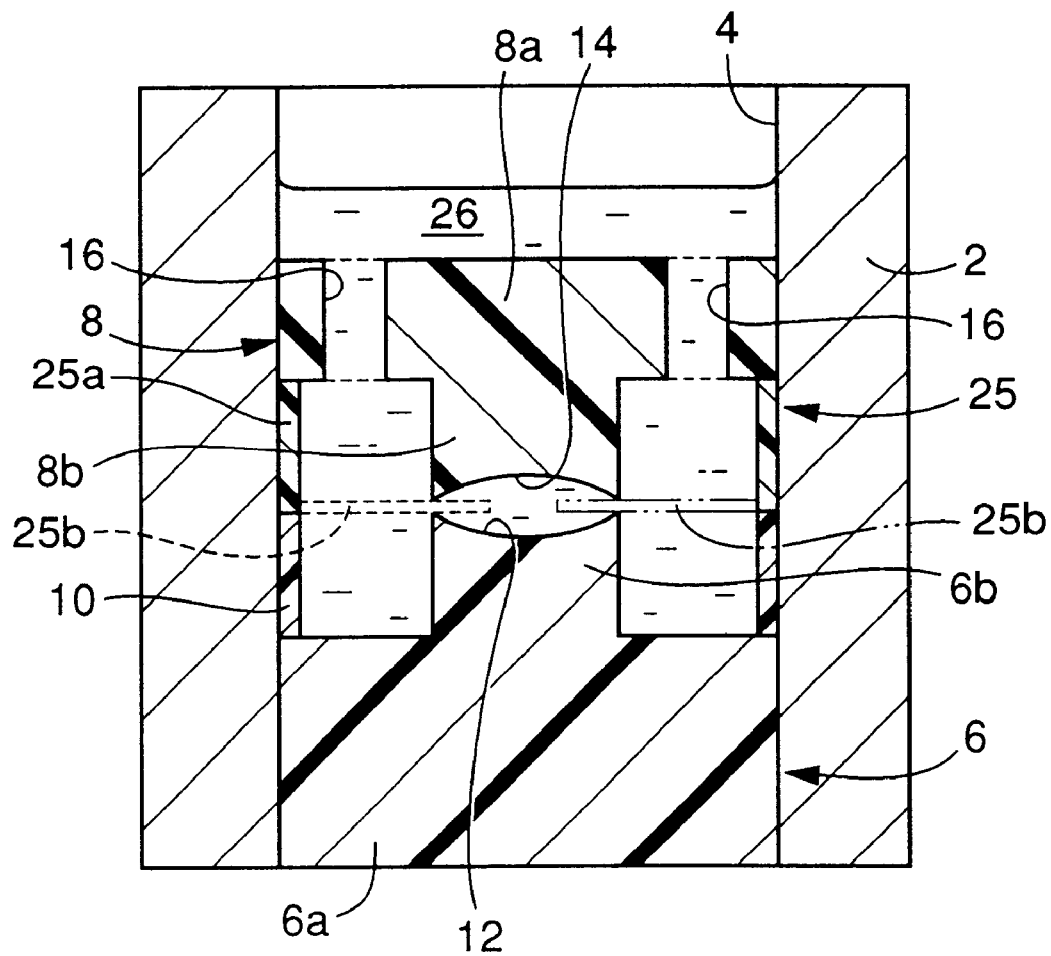
FIG. 7 is an elevational view in longitudinal or axial cross section showing the mold assembly filled with a monomer composition.

The insert member 25 may have, in addition to the inward projections 25*b,* 25*b,* a pair of balancers 25*c,* 25*c,* as shown in FIG. 6. The balancers 25*c* extend inwardly from two diametrically opposite positions of the inner circumferential surface of the cylindrical wall portion 25*a,* which two diametrically opposite positions are intermediate between the positions of the two inward projections 25*b,* 25*b,* in the circumferential direction of the insert member 25. The balancers 25*c* have a configuration similar to that of the inward projections 25*b.* The thus formed balancers 25*c* are effective to adjust the flow of the monomer composition in the mold assembly, permitting a uniform or even and symmetrical flow of the monomer composition, so that the intraocular lens to be obtained has improved quality consistency. Since the balancers 25*c* do not constitute any part of the intraocular lens to be obtained, the length of the balancers 25*c* is determined so as not to extend into the mold cavity 22 that gives the lens body 32 of the intraocular lens.

In forming the intraocular lens by using the thus constructed mold assembly, the mold cavity 22 and the intermediate chamber 18 are filled with a liquid monomer composition 26 which gives the workpiece for the intraocular lens. The monomer composition 26 is also accommodated in the upper chamber 20. The monomer composition 26 is polymerized by a method known in the art such as thermal polymerization or photopolymerization, whereby the polymerization product is obtained. As the monomer composition, at least one monomer is selected from among the above-described known monomers which are generally used in forming the intraocular lens. The monomer composition may include a conventionally used polymerization aid such as a polymerization initiator or a photosensitizer.

During the polymerization of the monomer composition 26 in the mold assembly, the volume of the monomer composition 26 decreases due to shrinkage thereof. In the present arrangement, however, the monomer composition 26 is supplied to the mold cavity 22 from the intermediate chamber 18 and the upper chamber 20 via the through-holes 16, whereby the mold cavity 22 is filled with the monomer composition 26 without suffering from otherwise possible shortage of the monomer composition due to its shrinkage during the polymerization. In the present mold assembly, the mold cavity 22 and the intermediate chamber 18 can be deaerated via the through-holes 16 formed in the cylindrical base portion 8*a* of the upper mold half 8. During the polymerization of the monomer composition 26, the upper opening of the inner bore 4 of the cylindrical body 2 may be desirably closed by a suitable lid member for the purpose of preventing evaporation of the monomer composition 26 during its polymerization.

Figure 8B:
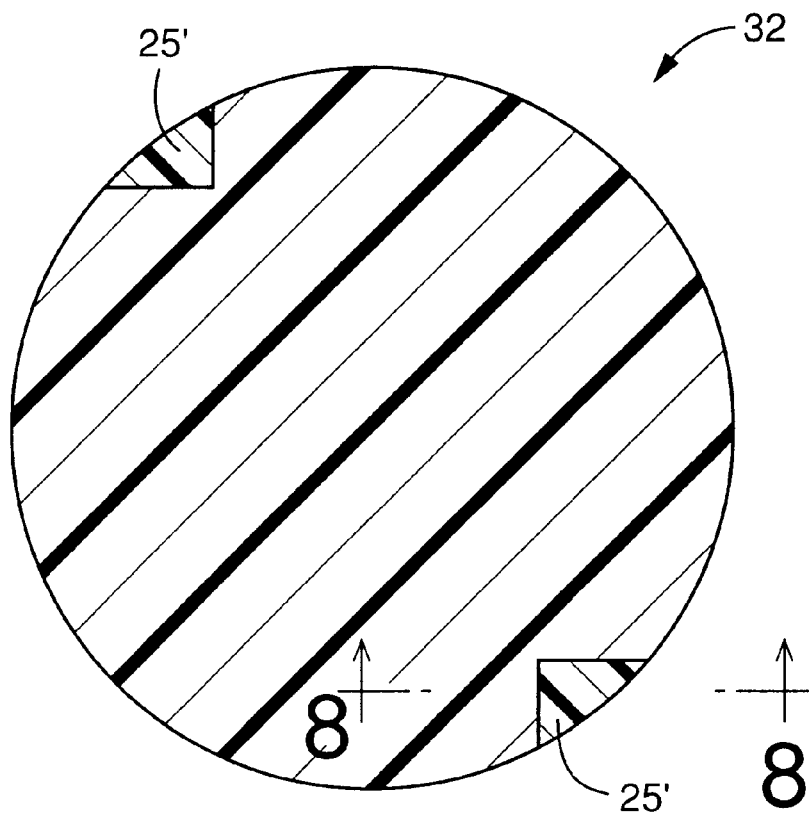
FIG. 8(b) is a transverse cross sectional view of the lens body of FIG. 8(a)
Figure 9A:
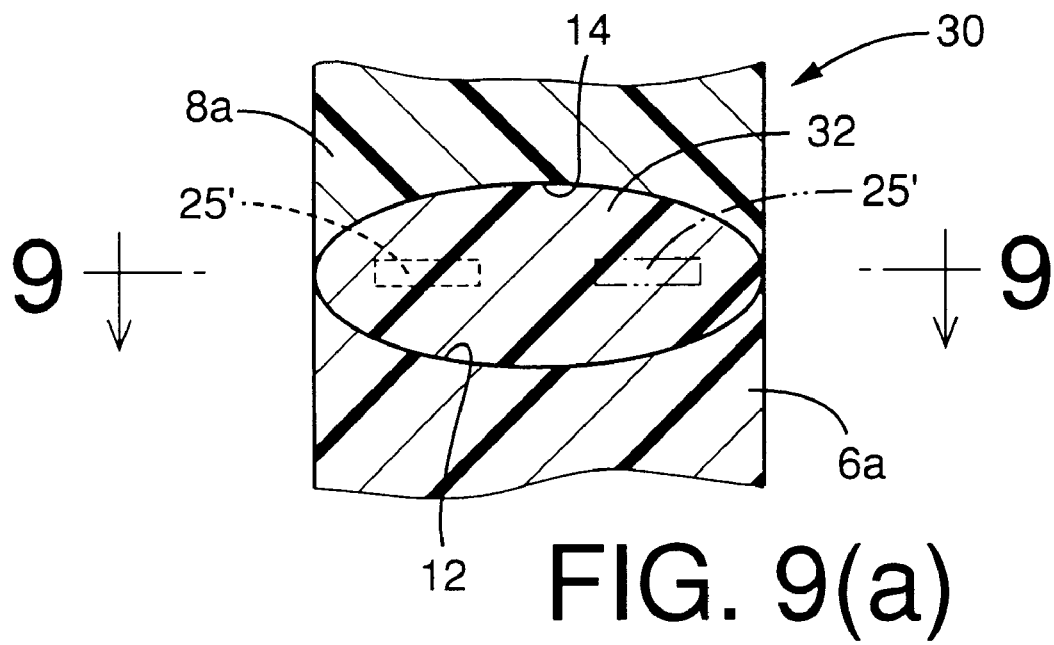
FIG. 9(a) is a longitudinal cross sectional view showing a cylindrical workpiece, which is cut from a polymerization product in a manner different from that of FIG. 8(a)
Figure 9B:
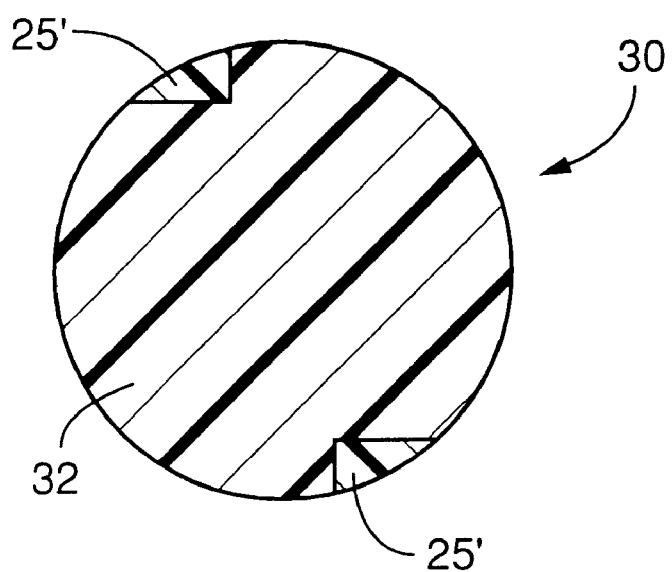
FIG. 9(b) is a transverse cross sectional view of the workpiece of FIG. 9(a), taken along line 9—9 of FIG. 9(a)

By thus polymerizing the monomer composition 26 filled in the mold assembly, the polymerization product which includes the upper and lower mold halves 8, 6 is obtained. The thus obtained polymerization product including the upper and lower mold halves 8, 6 is initially forced to be ejected from the cylindrical body 2. The polymerization product ejected from the cylindrical body 2 may be used as the workpiece which is subjected to a cutting operation to obtain the lens body 32 after the upper mold half 8 is removed from the polymerization product. Alternatively, the polymerization product including the upper and lower mold halves 8, 6 may be directly used as the workpiece to be cut into the lens body 32. In the former case, the workpiece is subjected to a cutting operation on its outer circumferential surface until the circumferential surface being cut becomes substantially flush with the outer circumferential surface of the upper cylindrical molding portion 6*b* of the lower mold half 6. Namely, the workpiece is machined until its diameter becomes substantially equal to the diameter of the upper cylindrical molding portion 6*b,* which is equal to the diameter of the lens body 32 to be obtained. Subsequently, the lower mold half 6 is removed from the cut workpiece, to thereby obtain the lens body 32 having the intended configuration as shown in FIG. 8. In the cutting or machining operation, the portion of the insert member 25 which is located outside the mold cavity 22 is removed so that only the free end portion of each inward projection 25*b* is left in the lens body 32 as an insert 25', as shown in FIGS. 8(*a*) and 8(*b*). For facilitating the removal of the upper and lower mold halves 8, 6 from the cut workpiece, the cut workpiece is immersed in a solvent such as ethanol to an extent that the lens body 32 is impregnated with the solvent, and the mold halves 8, 6 are separated from the cut workpiece. Alternatively, the mold halves 8, 6 may be removed by application of a sufficient force away from each other, or the mold halves 8, 6 are removed while the lens body 32 is solidified by cooling.

Where the polymerization product including the upper and lower mold halves 8, 6 is directly used as the workpiece, the polymerization product is subjected to a cutting operation for removing its radially outer portion so as to obtain a cylindrical block 30 as shown in FIG. 9, which includes the upper and lower mold halves 8, 6, and has the same diameter as the lens body 32 to be eventually obtained. Subsequently, the upper and lower mold halves 8, 6 are removed from the block 30, whereby the lens body 32 having the insert 25' and the intended configuration shown in FIG. 8 is obtained.

The thus obtained lens body 32 has, at its central portion, an optical portion, the entirety of which is formed of the polymer obtained by polymerization of the monomer composition. In the radially outer or peripheral portion of the thus obtained lens body 32, the distal end portions of the inward projections 25*b,* 25*b* of the insert member 25 are integrally embedded as the inserts 25' at the two positions which are opposite to each other diametrically of the lens body 32, as shown in FIG. 8(*b*). Namely, the lens body 32 includes the inserts 25' integrally embedded at the two diametrically opposite positions in the peripheral portion, so that mounting holes 34 are formed in these inserts 25' as shown in FIGS. 10(*a*) and 10(*b*) and explained below. In the present embodiment wherein the thickness of each inward projection 25*b* is made smaller than that of the radially outer or peripheral portion of the lens body 32, the distal or free end portion of each inward projection 25*b* integrally embedded in the peripheral portion of the lens body 32 is located at the axially intermediate portion of the lens body 32, that is, an intermediate portion of the lens body 32 as seen in the thickness direction, as shown in FIG. 10(*a*).

The thus obtained lens body 32 is formed with the mounting holes 34 in which support members 36 described below are partly inserted. Described in detail by referring to FIGS. 10(*a*) and 10(*b*), the mounting holes 34 are formed by using a suitable tool such as a drill, in the inserts 25' integrally embedded in the lens body 32. Each mounting hole 34 has a relatively small diameter and extends inwardly from the exposed surface of the insert 25'. The mounting holes 34 may be formed in the inserts 25' before the lower mold half 6 or the two mold halves 6, 8 is/are removed from the cut workpiece or the block 30.

Figure 11:
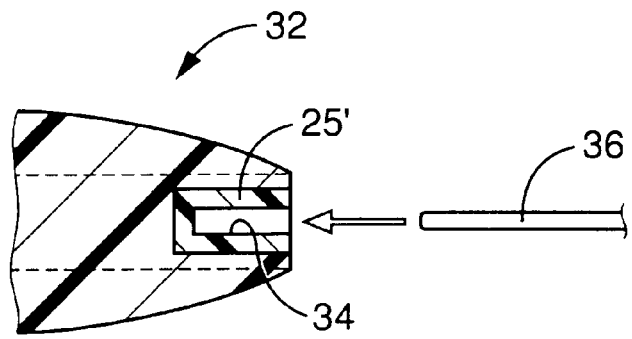
FIG. 11 is a fragmentary longitudinal cross sectional view showing a step of inserting a support member into the mounting hole.

The support members 36, 36 separately prepared from the lens body 32 are respectively inserted at their proximal or fixed end portions into the mounting holes 34, 34 formed in the inserts 25' in the lens body 32, as shown in FIG. 11. The material and configuration of the support members 36 are not particularly limited. The support members 36 may be formed of any known materials, and have various configurations known in the art. It is preferable to use, in the present embodiment, support members having a curved configuration such as a J-shaped configuration and formed of a thermoplastic synthetic resin material such as polyvinylidene fluoride. For permitting easy fabrication of the support members 36 and easy insertion thereof into the mounting holes 34, the proximal end portion of each support member 36 has a flat end face which is perpendicular to the center line of the mounting hole 34, for instance. Alternatively, the proximal end portion of the support member 36 may be tapered or have a semi-spherical shape.

Figure 12:
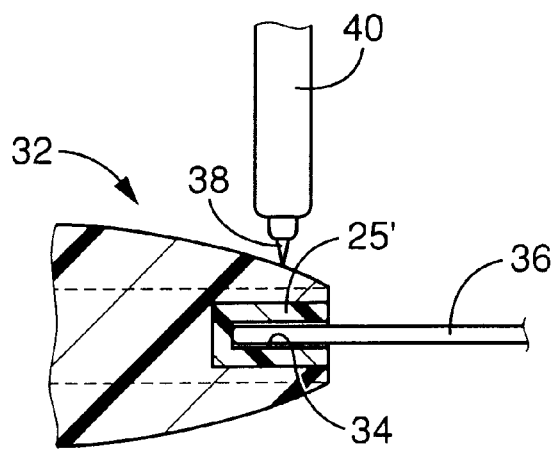
FIG. 12 is a longitudinal cross sectional view showing a step of welding the support member to the insert embedded in the lens body.

Each of the support members 36 inserted into the corresponding mounting hole 34 is fixed by heat-welding to the insert 25' integrally embedded in the lens body 32, to thereby provide the intended intraocular lens. In fixing each support member 36 to the insert 25' integrally embedded in the lens body 32, a welding device 40 having a pointed heat-generating portion 38 is used, as shown in FIG. 12. Described in detail, the heat-generating portion 38 of the welding device 40 is brought into contact with one of the part-spherical molded surfaces of the lens body 32, at its two diametrically opposite positions corresponding to the two inserts 25', whereby the heat generated by the heat-generating portion 38 of the welding device 40 is transmitted to the support members 36 inserted in the mounting holes 34 through the material of the lens body 32. Accordingly, the support members 36 are welded to the inner surfaces of the embedded inserts 25', which inner surfaces define the mounting holes 34.

Figure 13:
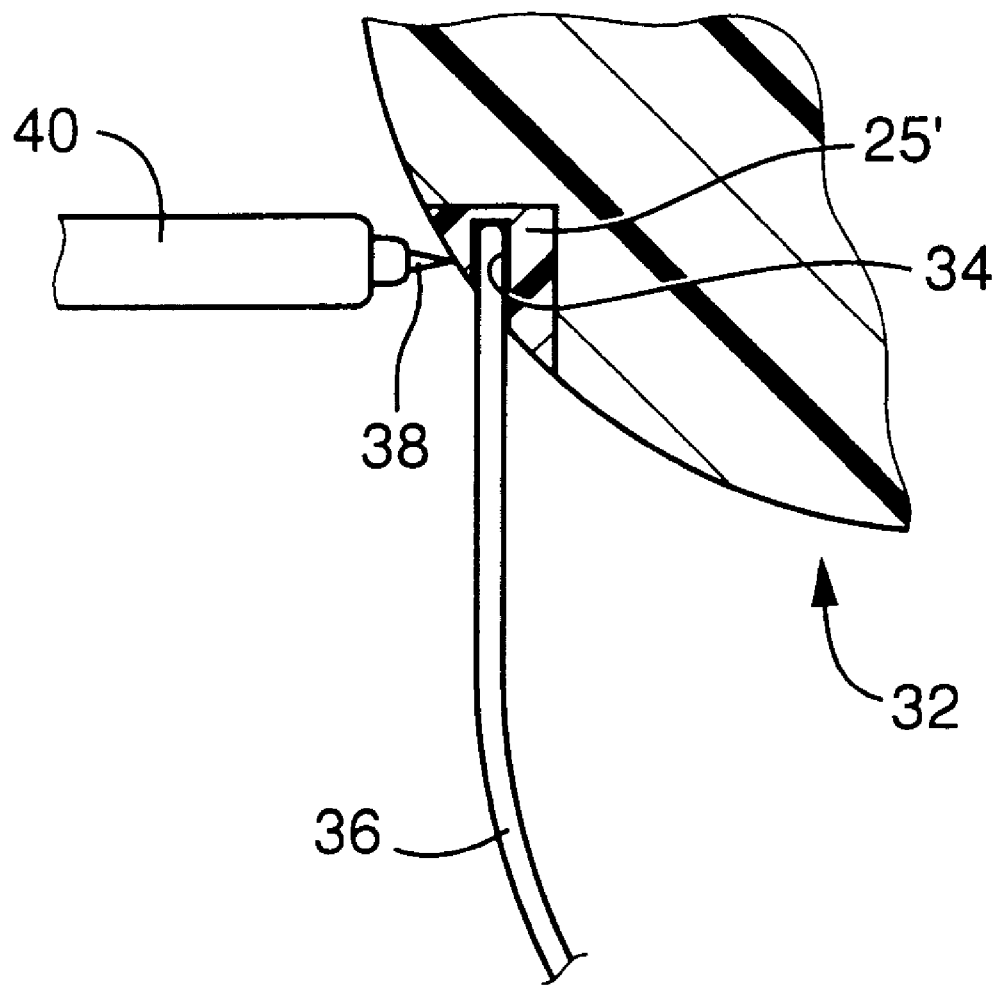
FIG. 13 is a fragmentary transverse cross sectional view showing another example of the step of welding the support member to the insert embedded in the lens body.

Each of the support members 36 may be otherwise fixed by heat-welding to the inner surfaces of the respective inserts 25' which define the mounting holes 34. According to one alternative method shown in FIG. 13, the heat-generating portion 38 of the welding device 40 is held in direct contact with the outer surface of the embedded inserts 25'. According to this method, the heat generated by the heat-generating portion 38 is transmitted to the support member inserted in the mounting hole 34 without passing through the material of the lens body 32.

Figure 14:
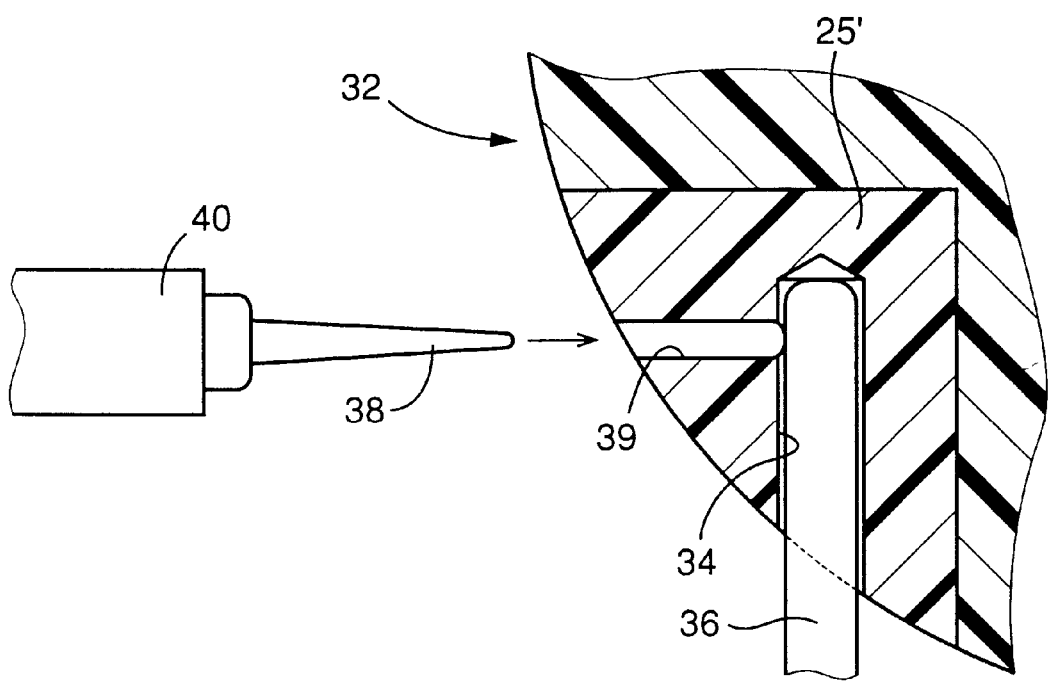
FIG. 14 is a fragmentary transverse cross sectional view showing still another example of the step of welding the support member to the insert embedded in the lens body.

According to another alternative method shown in FIG. 14, each insert 25' is provided with an access hole 39 which extends from its outer surface so as to intersect the mounting hole 34 at right angles. The heat-generating portion 38 of the welding device 40 is inserted into this access hole 39, to thereby directly heat the support member 36 in the mounting hole 34 for fixing the support member 36 by welding to the inner surfaces of the insert 25', which define the mounting hole 34. Though the heat-welding temperature varies depending upon the materials of the inserts 25' and the support members 36, it is preferably determined to be 100° C. or higher.

According to the present method of producing the intraocular lens described above, the support members 36, 36 are fixed to the polymer that constitutes the optical portion of the lens body 32, via the inserts 25' integrally embedded in the lens body 32. Accordingly, the optical portion is protected from adverse influences which would be caused when the support members were fixed directly to the polymer constituting the optical portion. In addition, the material of the insert member 25 (inserts 25') can be suitably selected so as to permit the support members 36 to be firmly fixed to the inserts 25', regardless of the material of the optical portion. Accordingly, the support members 36 can be fixed to the lens body 32 via the inserts 25' with high stability.

In the present embodiment, the support members 36 are fixed by heat-welding to the inserts 25' which are integrally embedded in the lens body 32. This arrangement avoids the problem of the residual monomer conventionally experienced where the monomer is used as an adhesive for bonding the support members to the lens body, whereby the obtained intraocular lens has high quality and high reliability.

While the present invention has been described in detail in its preferred embodiment, it is to be understood that the invention is not limited to the details of the illustrated embodiment, but may be otherwise embodied.

Figure 15:
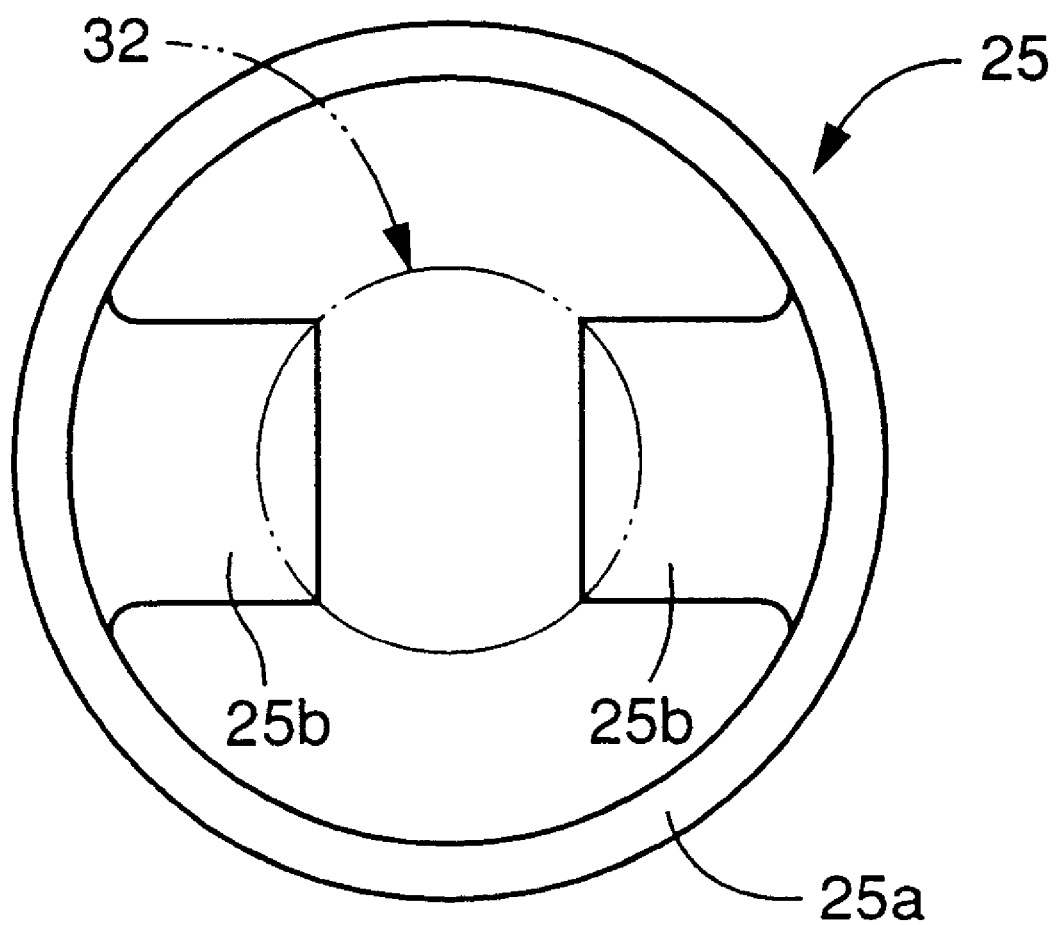
FIG. 15 is a plan view showing another example of the insert member used in producing the intraocular lens according to the present invention.
Figure 16A:
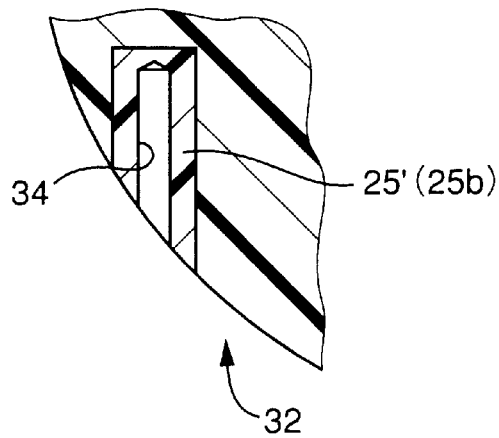
FIGS. 16(a)–16(d) are fragmentary transverse cross sectional views showing the lens body in which different forms of the insert are embedded.
Figure 16B:
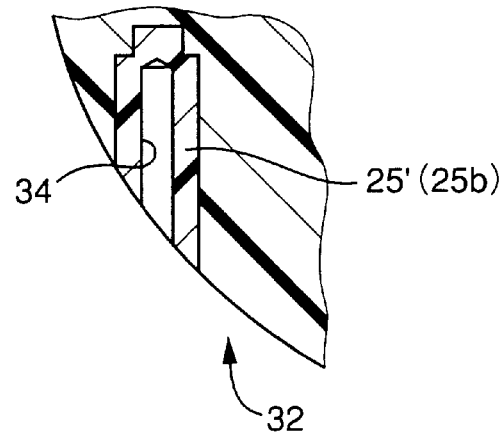
Figure 16C:
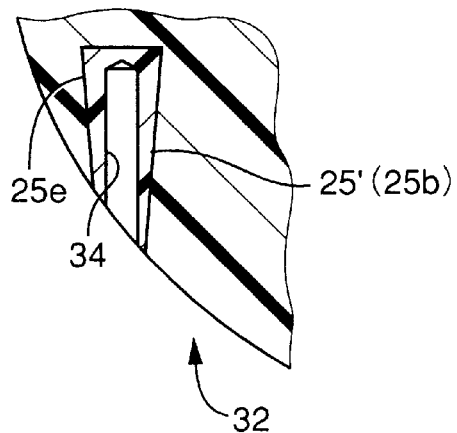
Figure 16D:
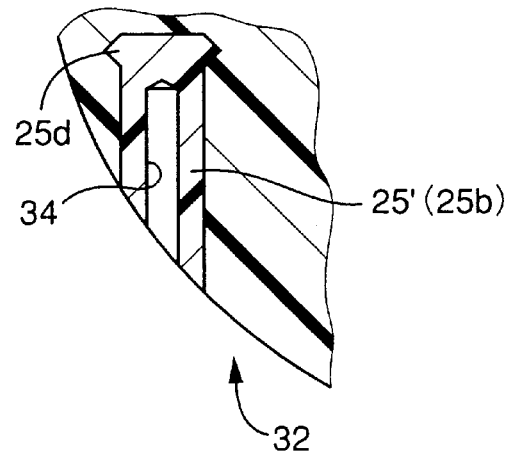

The inward projections 25b of the insert member 25 installed on the mold assembly may be otherwise shaped, provided that the inward projections 25b at least partly extend into the mold cavity 22 which gives the lens body 32. The inward projections 25b are preferably located in the mold assembly at the positions corresponding to the mounting hole regions of the lens body to be obtained, without reaching the optical portion of the lens body. For instance, the insert member 25 may have a pair of inward projections 25b, 25b as shown in FIG. 15, which are wide rectangular plates extending radially inwardly from the respective two diametrically opposite parts of the cylindrical wall portion 25a. The insert member 25 used in the present invention may have hollow inward projections 25b, each having a hole or bore which serves as the mounting hole in which the support member 36 is inserted. The configuration of the cylindrical wall portion 25a of the insert member 25, at which the insert member 25 is fitted in the inner circumferential surface of the cylindrical body 2 that defines the inner bore 4, is not limited to that of the illustrated embodiment, but may be modified depending upon the structure of the mold assembly.

The shape of the distal end portion of each inward projection 25b which is integrally embedded in the lens body 32 is not limited to the rectangular plate-like shape in the illustrated embodiment. For instance, the distal end portion of the inward projection 25b may have a circular cross sectional shape as shown in FIGS. 16(*a*) and 16(*b*). Alternatively, the distal end portion of the inward projection 25b may have a tapered outer circumferential surface 25e as shown in FIG. 16(*c*), wherein the outside diameter of the distal end portion is gradually reduced in the direction from the fixed end to the free end. Further, the distal end portion of the inward projection 25b may be provided with an annular protrusion 25d as shown in FIG. 16(*d*), which protrudes radially outwards from its outer circumferential surface. Each of the distal end portions shown in FIGS. 16(*c*) and 16(*d*) functions as anchoring means for anchoring the inserts 25' to the polymer that constitutes the optical portion of the lens body.

Figure 17:
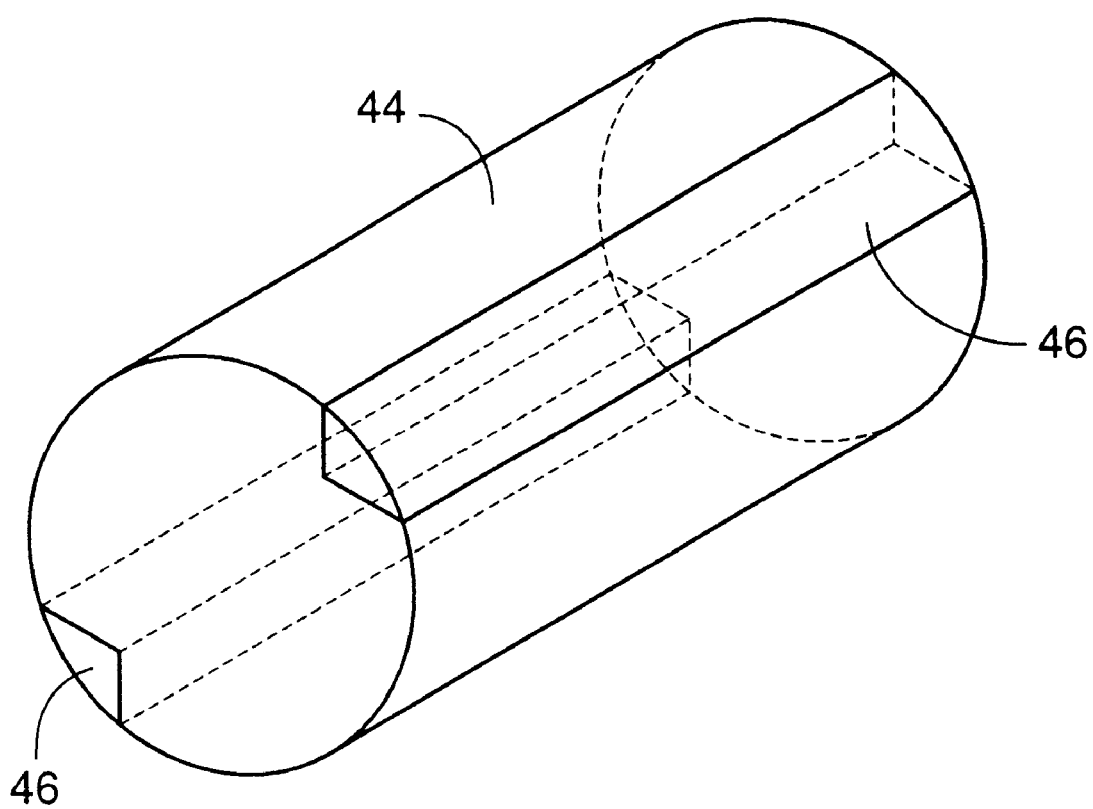
FIG. 17 is a perspective view showing a cylindrical lens blank which gives a plurality of lens bodies.

In the illustrated embodiment, the intraocular lens is produced by molding, using a mold assembly which defines a mold cavity giving a single lens body 32. The principle of the present invention is applicable to a method wherein a plurality of lens bodies are obtained by cutting a cylindrical lens blank 44 as shown in FIG. 17 into a plurality of pieces each having a suitable axial dimension. In this case, elongate insert members 46, 46 are integrally embedded at two diametrically circumferential sections of the peripheral portion of the cylindrical lens blank 44, such that the insert members 46 extend over the entire axial length of the cylindrical lens blank 44.

The structure of the mold assembly is not limited to that of the illustrated embodiment, but may be otherwise embodied. For instance, the cylindrical body 2 and the lower mold half 6 may be formed integrally with each other. At least one of the lower molding surface 12 and the upper molding surface 14 may be a curved convex surface.

To further clarify the present invention, there will be described some examples of the invention. It is to be understood that the present invention is not limited to the details of the illustrated examples, but may be otherwise embodied with various changes, improvements and modifications, which may occur to those skilled in the art, without departing from the scope of the attached claims.

There was prepared an intraocular lens by using a mold assembly shown in FIG. 1 in accordance with the process steps shown in FIGS. 1–12.

Initially, an insert member formed of cross-linked polymethyl methacrylate having a configuration shown in FIGS. 2 and 3 was molded by polymerization. This insert member was set in the mold assembly shown in FIG. 1. In the meantime, a monomer composition was prepared by using 70 parts by weight of phenoxyethyl acrylate, 30 parts by weight of ethyl acrylate, and 20 parts by weight of 2-hydroxyethyl methacrylate. The monomer composition was introduced into the upper chamber of the mold assembly, so as to fill the mold cavity shown in FIG. 7. After the mold assembly was deaerated in a vacuum oven, it was heated and held at 60° C. for 16 hours in an oven. Subsequently, the temperature in the oven was elevated from 60° C. to 130° C. at a rate of 10° C./hour, whereby the monomer composition in the mold assembly was polymerized.

The thus obtained polymerization product which integrally includes the upper and lower mold halves was forced to be ejected from the cylindrical body by using a hydraulic press. The ejected polymerization product as the workpiece was subjected to cutting operations to remove the base portions of the upper and lower mold halves, thereby providing a cylindrical block which integrally includes the cylindrical molding portions of the upper and lower mold halves. The circumferential surface of this block was then subjected to a cutting operation on a lathe, until the diameter of the block has become equal to the diameter of the lens body to be obtained. The thus cut cylindrical block includes the inserts 25' which are exposed on the cut circumferential surface. Subsequently, the cylindrical molding portions of the upper and lower mold halves were removed from the block, so that the lens body 32 shown in FIG. 8(b) is eventually obtained. This lens body 32 has a diameter of 6.0 mm and an edge thickness of 0.3 mm. The edge thickness is a thickness of the lens body at its outer circumferential surface on which the inserts 25' are exposed.

Figure 10A:
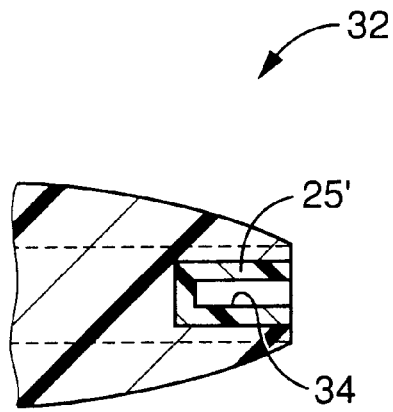
FIG. 10(a) is a fragmentary longitudinal cross sectional view showing the lens body in which a mounting hole is formed, the view being taken along line 10—10 in FIG. 10(b)
Figure 10B:
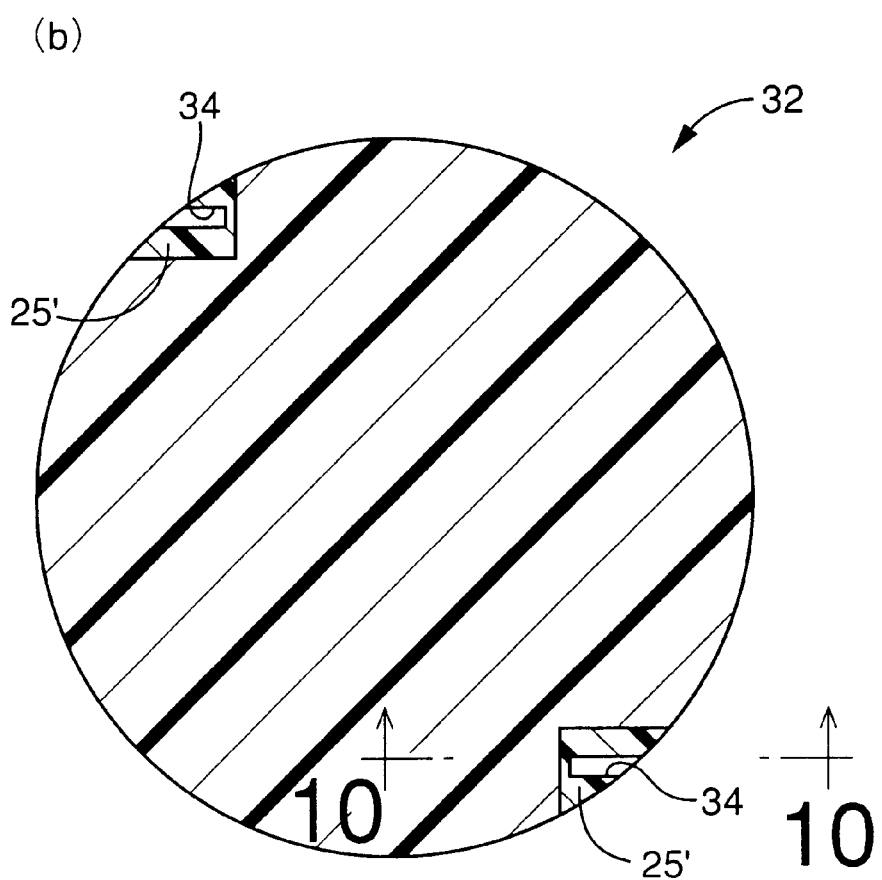
FIG. 10(b) is a transverse cross sectional view of the lens body of FIG. 10(a)

Mounting holes in which the support members are to be inserted were bored in the inserts 25' integrally embedded in the lens body 32, as shown in FIGS. 10(a) and 10(b). Each mounting hole has a diameter of 0.15 mm and a depth of 0.5 mm. To each of the thus formed mounting holes, the fixed end portion of the separately prepared support member formed of polyvinylidene fluoride was inserted (FIG. 11). The support member was welded to the inner surfaces of the embedded insert which defines the mounting hole, by using a heat-welding device shown in FIG. 12, whose heat-generating portion 38 was heated to 600° C. Described more specifically, the end of the heat-generating portion was brought into contact with one of the opposite part-spherical molded surfaces of the lens body at one of the two diametrically opposite portions corresponding to the mounting hole region of the lens body in which the insert was integrally embedded. Thus, the support member was firmly fixed to the lens body via the insert, to thereby provide the intended intraocular lens.

The thus obtained intraocular lens was visually inspected. It was confirmed that the surfaces of the optical portion of the intraocular lens were not deformed. Further, the optical properties such as the resolution power was not deteriorated. An experiment was conducted on the intraocular lens to examine the strength of bonding of the support members to the lens body, by applying a 20 g load for one minute to the two support members in a direction away from each other. The result of the experiment showed that the support members were firmly secured to the lens body.

An experiment similar to that in the above Example 1 was conducted, except that the insert member formed of cross-linked polymethyl methacrylate was replaced with an insert member formed of polyvinylidene fluoride.

The visual inspection of the intraocular lens showed that the intraocular lens had an optical portion whose surfaces were not deformed. The optical properties were not deteriorated. Further, the result of the experiment similar to that in the above Example 1 revealed that the support members were firmly fixed to the lens body with high stability.

What is claimed is:

1. An intraocular lens including a lens body given by polymerization of a monomer composition in a mold cavity of a mold assembly and having an optical portion at a central portion thereof and a support member partly inserted into a mounting hole which is open in a circumferential surface of said lens body, so that said support member is fixed with respect to said lens body, wherein the improvement comprises:

said monomer composition being polymerized to give said lens body with an insert being set in the mold assembly, said insert being impregnated with said monomer composition, so that said monomer composition is absorbed by or swollen in said insert whereby said insert, is integrally fixed or bonded to said lens body without applying a bonding adhesive therebetween, said insert being embedded in said lens body such that said insert is exposed to said circumferential surface of said lens body, said mounting hole being formed in said insert.

2. An intraocular lens according to claim 1, wherein said insert has means for preventing said insert from being removed from said lens body.

3. An intraocular lens according to claim 1, wherein said insert is formed of polyalkyl methacrylate.

4. An intraocular lens according to claim 1, wherein said insert is formed of cross-linked polymethyl methacrylate.

5. An intraocular lens according to claim 1, wherein said insert is substantially flush with said circumferential surface of said lens body.

6. An intraocular lens according to claim 1, wherein said insert is free of any holes other than said mounting hole.

* * * * *